(12) United States Patent
Sarntinoranont et al.

(10) Patent No.: US 9,629,943 B2
(45) Date of Patent: *Apr. 25, 2017

(54) APPARATUS AND METHODS FOR BLOCKING NEEDLE AND CANNULA TRACTS

(71) Applicant: University of Florida Research Foundation, Gainesville, FL (US)

(72) Inventors: Malisa Sarntinoranont, Gainesville, FL (US); Christopher Batich, Gainesville, FL (US); Bradley Jay Willenberg, Orlando, FL (US); Erik Hagel, Stokholm (SE); Louis C. Vazquez, Brandon, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/159,075

(22) Filed: May 19, 2016

(65) Prior Publication Data

US 2016/0263290 A1  Sep. 15, 2016

Related U.S. Application Data

(63) Continuation of application No. 13/503,778, filed as application No. PCT/US2010/057938 on Nov. 24, 2010, now Pat. No. 9,370,626.

(Continued)

(51) Int. Cl.
*A61L 31/10* (2006.01)
*A61L 31/16* (2006.01)
(Continued)

(52) U.S. Cl.
CPC .......... *A61L 31/10* (2013.01); *A61B 10/0233* (2013.01); *A61L 31/145* (2013.01);
(Continued)

(58) Field of Classification Search
CPC ......... A61L 2300/606; A61L 2300/608; A61B 2017/00898
See application file for complete search history.

(56) References Cited

U.S. PATENT DOCUMENTS 5,254,105 A   10/1993   Haaga
5,906,631 A   5/1999    Imran
(Continued)

OTHER PUBLICATIONS

Kallmes, et al., "In Vivo Evaluation of a New Type 1 Collagen Hemostatic Plug for High Risk, large-core biopsies," JVIR 9 (1998) pp. 656-659.
(Continued)

*Primary Examiner* — Nathan R Price
*Assistant Examiner* — Melissa A Snyder
(74) *Attorney, Agent, or Firm* — Thomas | Horstemeyer, LLP

(57) ABSTRACT

Apparatus and methods for blocking needle tracts are disclosed. In some embodiments, the needle tracts are blocked by using a needle that includes an elongated shaft that defines an outer surface, and a polymer coating applied to the outer surface of the shaft, the coating being adapted to block the tract formed by insertion of the needle into an object.

20 Claims, 4 Drawing Sheets

Related U.S. Application Data

(60) Provisional application No. 61/355,391, filed on Jun. 16, 2010, provisional application No. 61/295,351, filed on Jan. 15, 2010, provisional application No. 61/264,541, filed on Nov. 25, 2009, provisional application No. 61/264,098, filed on Nov. 24, 2009.

(51) Int. Cl.
  *A61M 5/32* (2006.01)
  *A61M 25/00* (2006.01)
  *A61B 10/02* (2006.01)
  *A61L 31/14* (2006.01)
  *A61M 5/158* (2006.01)
  *A61B 17/00* (2006.01)

(52) U.S. Cl.
  CPC .......... *A61L 31/16* (2013.01); *A61M 5/158* (2013.01); *A61M 5/32* (2013.01); *A61M 25/0045* (2013.01); *A61B 2017/00898* (2013.01); *A61L 2300/606* (2013.01); *A61L 2420/08* (2013.01)

(56) References Cited

U.S. PATENT DOCUMENTS

| | | | |
|---|---|---|---|
| 6,071,301 A | 6/2000 | Cragg et al. | |
| 6,200,328 B1 | 3/2001 | Cragg et al. | |
| 6,270,484 B1 | 8/2001 | Yoon | |
| 6,280,399 B1 | 8/2001 | Rossin et al. | |
| 6,334,216 B1 | 12/2001 | Barth | |
| 6,592,608 B2 | 7/2003 | Fisher et al. | |
| 6,605,294 B2 | 8/2003 | Sawhney | |
| 6,610,046 B1 | 8/2003 | Usami et al. | |
| 6,790,185 B1 | 9/2004 | Fisher et al. | |
| 6,840,952 B2 | 1/2005 | Saker et al. | |
| 6,969,373 B2 | 11/2005 | Schwartz et al. | |
| 7,501,179 B2 | 3/2009 | Song et al. | |
| 2001/0002411 A1 | 5/2001 | Ronan et al. | |
| 2004/0030282 A1 | 2/2004 | Freyman et al. | |
| 2006/0025815 A1 | 2/2006 | McGurk et al. | |
| 2006/0188546 A1* | 8/2006 | Giroux | A61L 27/34 424/426 |
| 2006/0204535 A1 | 9/2006 | Johnson | |
| 2007/0005024 A1 | 1/2007 | Weber et al. | |
| 2007/0088295 A1 | 4/2007 | Bankiewicz | |
| 2007/0129757 A1 | 6/2007 | Armstrong | |
| 2007/0276340 A1 | 11/2007 | Poston et al. | |
| 2009/0105768 A1* | 4/2009 | Cragg | A61B 17/70 606/301 |
| 2009/0318746 A1 | 12/2009 | Thurmond, II et al. | |

OTHER PUBLICATIONS

Engeler, et al., "Pneumothorax after Lung Biopsy: Prevention with Transpleural Placement of Compress Collagen Foam Plugs," Radiology 184 (1992) pp. 787-789.

International Search Report and Written Opinion dated Jan. 26, 2011.

* cited by examiner

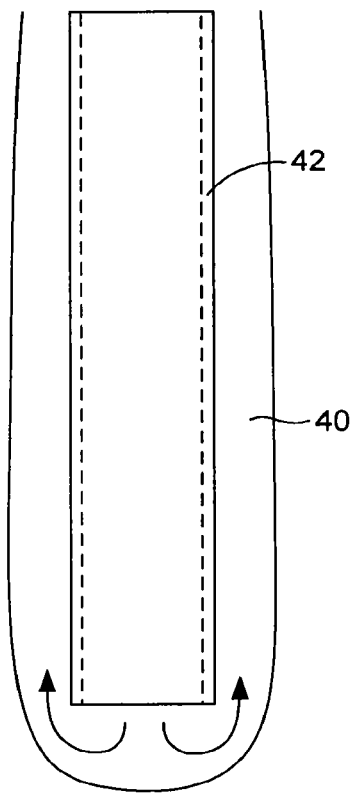
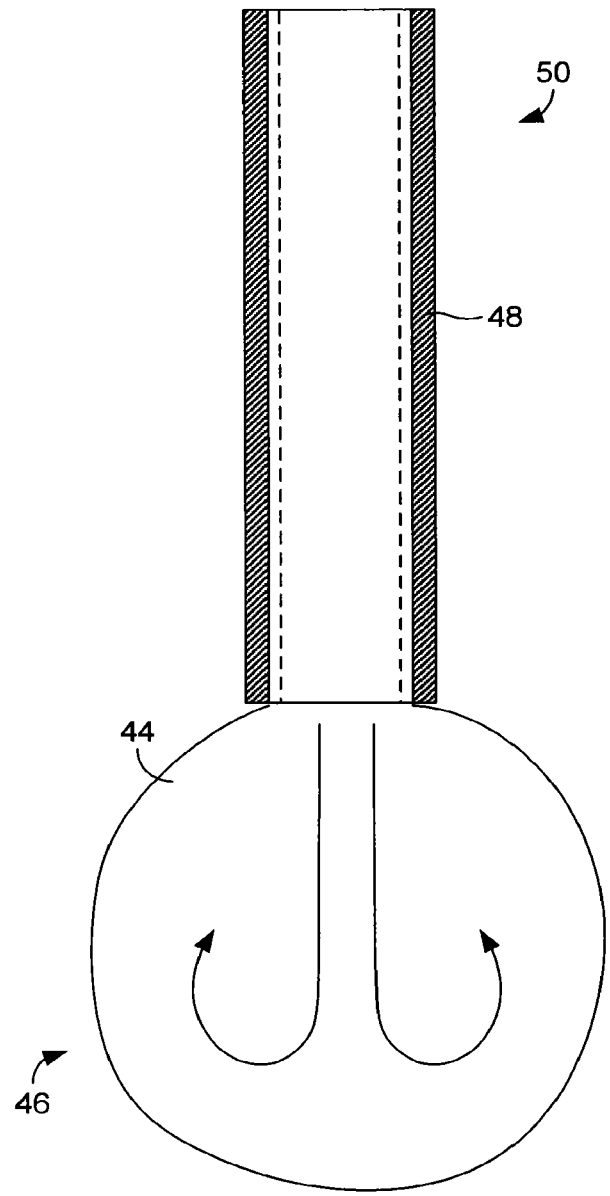
FIG. 4
(PRIOR ART)
FIG. 5

APPARATUS AND METHODS FOR BLOCKING NEEDLE AND CANNULA TRACTS

CROSS-REFERENCE TO RELATED APPLICATIONS

This application is a continuation of and claims priority to U.S. non-provisional application entitled "Apparatus and Method for Blocking Needle and Cannula Tracts" having Ser. No. 13/503,778, filed Apr. 24, 2012, which is a National Stage of PCT Application entitled "Apparatus and Method for Blocking Needle and Cannula Tracts" having serial number PCT/US10/57938, filed Nov. 24, 2010, which claims priority to U.S. provisional application entitled "Blocking Needle Tracks to Prevent Unwanted Movement of Cells After Biopsy or Backflow of Drugs During Infusions" having Ser. No. 61/264,098, filed Nov. 24, 2009, U.S. provisional application entitled "Coatings to Prevent Backflow" having Ser. No. 61/264,541, filed Nov. 25, 2009, U.S. provisional application entitled "Effect of Polymer Coated Needles on Infusate Backflow During Convection-Enhanced Delivery" having Ser. No. 61/295,351, filed Jan. 15, 2010, and U.S. provisional application entitled "Drug Delivery Devices and Methods for Delivering a Drug to a Patient Tissue" having Ser. No. 61/355,391, filed Jun. 16, 2010, each of which are entirely incorporated herein by reference.

FEDERAL SPONSORSHIP

This invention was made with Government support under Contract/Grant No. NIH R01 NS063360, awarded by the National Institutes of Health. The Government has certain rights in this invention.

BACKGROUND

In various medical procedures, a needle or cannula is introduced into the body, either for the purpose of removing tissue or delivering a substance to the tissue. An example of the former situation is fine needle aspiration needle biopsy (FNAB) in which a needle is inserted into an organ (e.g., the liver, lung, brain, thyroid) and cells are removed for the purpose of diagnosing a condition, such as cancer. An example of the latter is convection-enhanced delivery (CED) in which drugs are continuously infused into the brain tissue using a cannula.

Whether the needle or cannula is used to remove tissue or deliver a substance to the tissue, it is desirable to prevent travel of the tissue or substance along the pathway formed by the needle or cannula. For instance, in cases in which cancer cells are being removed in a biopsy procedure, it is desirable to prevent the spread of such cells to other parts of the patient's tissue when the biopsy needle is withdrawn. In the case of drug delivery, it is desirable to prevent the drug from flowing backwards along the pathway formed by the delivery cannula. Unfortunately, it is difficult to ensure that such unintended results do not happen. For instance, drug backflow is common when high infusion rates are used.

In view of the above discussion, it can be appreciated that it would be desirable to have an apparatus and method for blocking needle and cannula tracts to prevent the migration of patient tissue and/or delivered substances within the body.

BRIEF DESCRIPTION OF THE DRAWINGS

The disclosed apparatus and methods can be better understood with reference to the following drawings. The components in the drawings are not necessarily drawn to scale.

FIG. 4 is a partial side view of a conventional uncoated needle in use during drug infusion.

FIG. 5 is a partial side view of a coated needle in use during drug infusion.

DETAILED DESCRIPTION

As described above, it would be desirable to have an apparatus and method for blocking needle and cannula tracts to prevent the migration of patient tissue and/or delivered substances within the body. As described below, such migration can be prevented or at least reduced by coating the needle or cannula with a biocompatible polymer that blocks or seals the pathway or tract formed by the needle or cannula. When the tract is sealed, migration of patient cells during a biopsy procedure is prevented or reduced. Similarly, sealing of the tract also prevents or reduces backflow of drugs that are infused into patient tissue. In some embodiments, the polymer coating rapidly swells when it contacts patient tissue. In some embodiments, the coating comprises a dual layer coating having an inner layer comprised of a first material and an outer layer comprised of a second material. By way of example, the inner layer can comprise polyethylene oxide (PEO) and sodium alginate and the outer layer can comprise polyvinyl alcohol (PVA).

In the following disclosure, various embodiments are described. It is to be understood that those embodiments are merely example implementations of the disclosed inventions. Accordingly, Applicant does not intend to limit the present disclosure to those particular embodiments. For purposes of brevity and convenience, the term "needle" is used in this disclosure to describe both what are conventionally designated as needles and other rigid tubular members that are inserted into the body, such as cannulas. Although the discussion that follows focuses on convection-enhanced delivery, it is noted that this procedure is only cited as an example for purposes of convenience in describing the disclosed inventions.

Convection-enhanced delivery (CED) involves the continuous infusion of drugs via needles into the central nervous system (CNS). The technique enables convective distribution of high drug concentrations to the target tissue without systemic toxicity. The therapeutic delivery method has the potential to increase and enhance the treatment of nervous system diseases, such as neurodegenerative diseases, Parkinson's disease, cancerous tumors, and other CNS diseases. CED has the potential of enabling the delivery of high molecular weight compounds such as therapeutic agents, gene vectors, and immunotoxins by convectional transport.

Figure 1:
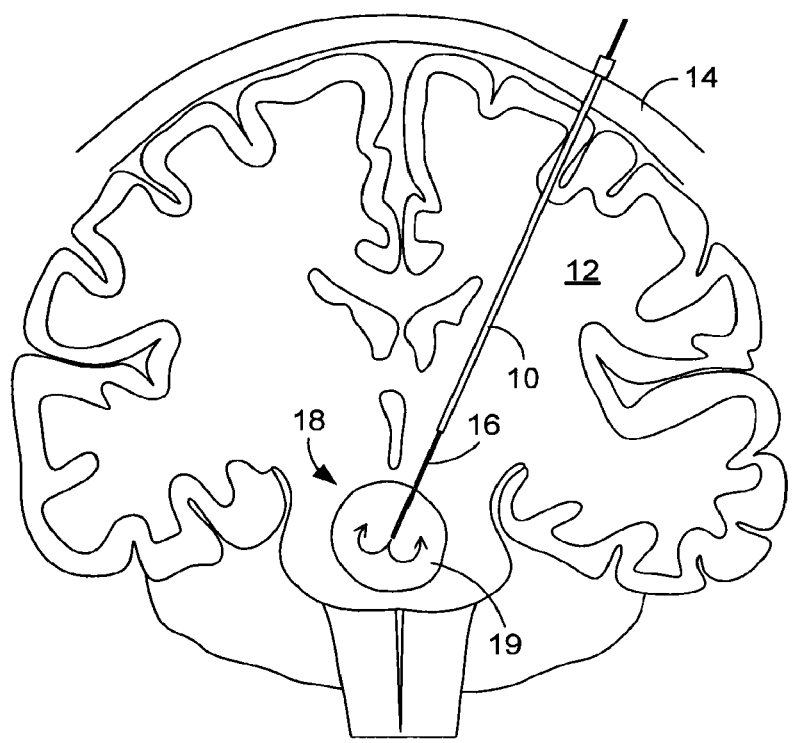
FIG. 1 is schematic front view of a patient's brain during a drug infusion procedure.

FIG. 1 illustrates an example of CED. As shown in that figure, a guide tube 10 is inserted into the brain 12 via a passage formed through the skull 14. Once the guide tube 10 has been inserted, an elongated needle 16 can be passed through the tube to a target site 18. An infusion pump (not shown) is connected to the needle 16 and is used to drive the infusate 19 directly into the target site 18. The pressure forces of the infusate 19 dilate the target tissue, which possibly enhances the penetration of the drug. Because the needle 16 bypasses the blood brain barrier (BBB), larger molecule drugs can be distributed than with more conventional drug administration.

It is important that the infusate 19 remains at the target site 18 and does not migrate to other areas of the brain 12, such as back along the pathway formed by the needle 16. Such backflow along the needle tract is more likely when higher infusion rates are used. When a higher infusion rate is used, the infused drug can be forced up along the needle tract due to high pressure forces at the infusion site. Although reduction in the rate of infusion can reduce pressure at the infusion site and thereby reduce backflow, infusion rate reduction translates into longer treatment times for the patient.

Figure 2:
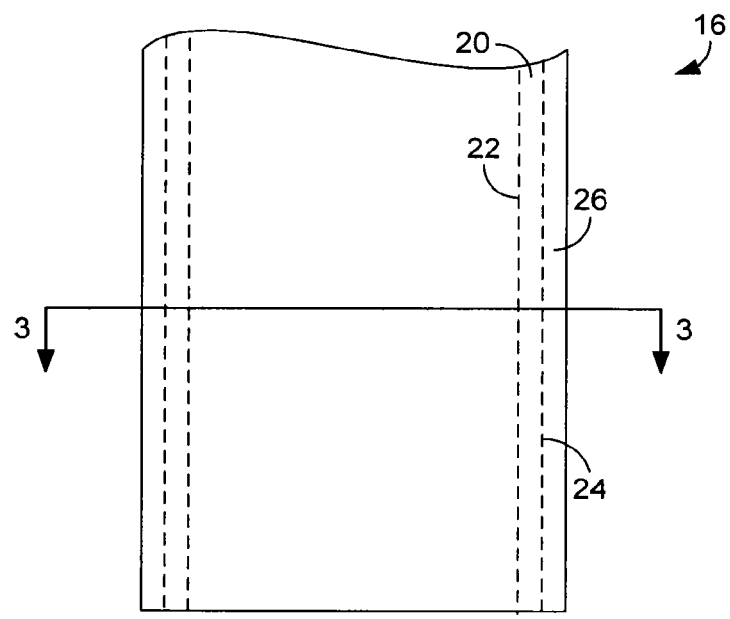
FIG. 2 is a partial side view of a needle used in the procedure illustrated in FIG. 1.

It has been determined that backflow of the type described above can be prevented or reduced by coating the needle 16 with a biocompatible polymer that blocks or seals the tract formed by the needle. FIG. 2 illustrates an example embodiment of such a coated needle 16. As shown in the figure, the needle 16 comprises an elongated rigid shaft 20 having an inner surface 22 that defines an inner lumen of the shaft and an outer surface 24 on which a biocompatible polymer coating 26 is provided. By way of example, the shaft 20 is composed of a silica material or a metal material, such as steel. In some embodiments, the shaft 20 is cylindrical and has an outer diameter ranging from approximately 0.2 to 2.11 millimeters (mm).

In some embodiments, the polymer coating 26 comprises one or more water-soluble polymers that swell when they contact patient tissue to form a hydrogel. Hydrogels are polymer materials that contain a three-dimensional network of covalent crosslinked hydrophilic polymer chains. The swelling behavior results from thermodynamic forces, which reach equilibrium when the hydrogel reaches the swollen state. Due to their high water content, many hydrogels possess excellent biocompatibility. For instance, hydrogel mechanical properties, such as flexibility and shape, are similar to those of human tissue.

Polymers appropriate for the formation of the coating 26 include polyethylene oxide (PEO), sodium alginate, polyvinyl alcohol (PVA), polyvinylpyrrolidone (PVP), and dextran. PEO is a nontoxic polymer and has been approved by the Food and Drug Administration (FDA) for use in biomedical applications. PEO can be made by several different methods, including chemical cross-linking, radiation cross-linking, copolymerization with other polymers, and ring opening polymerization. The monomer can be produced by oxidation of ethylene by either air or oxygen to form an ethylene oxide ring. The epoxide ring is the simplest cyclic ether with the formula $C_2H_4O$. Through anionic ring-opening polymerization in the presence of a catalyst, the ethylene oxide ring opens and PEO is formed.

PEO hydrogels are among the most suitable hydrogels for biomedical applications because of their nontoxicity and high biocompatibility and due to the presence of a cross-linker within the polymer chain. The amount of crosslinking affects the properties of the polymer, and therefore the swelling behavior and the solid/liquid state of the polymer. The swelling rate is dependent on the molecular weight and the concentration of the polymer in water and the network structure of the polymer.

Sodium alginate is a linear polysaccharide composed of two monomers β-(1-4)-linked D-mannuronic acid (M) and α-(1-4)-linked L-guluronic acid (G). The monomeric units are extracted from native brown seaweed. The copolymer is composed of block or alternating monomer units. It is the ion binding properties that causes polysaccharide to gel. The adsorption of water is due to the carboxylic and hydroxyl groups. The polarity of these groups creates hydrogen bonds with water. The sodium molecules are bonded to the oxygen ions on the carboxylic groups. Adding $Ca^{2+}_2$ makes alginate solutions gel rapidly via the creation of ionic crosslinks mainly between the carboxylic acid groups on nearby chains by electrostatic forces. The calcium ions exchange with the sodium ions and create a polymer hydrogel with advantageous characteristics.

PVA hydrogels are biocompatible materials with water adsorption properties. PVA hydrogel is hydrophilic and has similar mechanical properties as human tissue and is therefore appropriate for biomedical applications. Although PVA is similar to PEO, PVA has a hydroxyl group attached to the main chain instead of an oxygen atom within the main chain. The functional hydroxyl group within PVA provides its swelling capabilities and water adsorption properties. It is the hydrogen bonding to water that makes PVA swell. PVA can also be used as a base polymer after substitution of the hydroxyl group with various functional groups.

The structure of PVP has characteristics similar to proteins and can be precipitated by protein precipitators. PVP is also soluble in water and is hydrophilic.

Dextran hydrogels exhibit low tissue toxicity and high enzymatic degradability at desired sites. Dextran hydrogels may be appropriately used as a potential matrix system for specific delivery and/or controlled release of bioactive agents. Dextran hydrogels can be obtained by several different approaches.

Figure 3A:
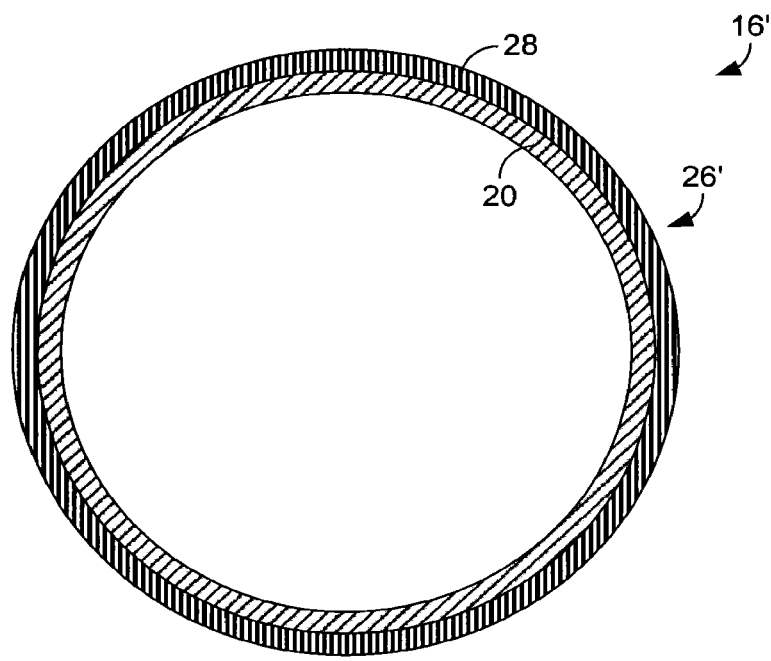
FIG. 3A is a cross-sectional view of a first embodiment for the needle of FIG. 2 taken along line 3-3.

FIG. 3A illustrates a first example coated needle 16'. In this embodiment, the shaft 20 is provided with a coating 26' that comprises a single layer 28 of water-soluble polymer. By way of example, the polymer is selected from the group comprising or consisting of PEO, sodium alginate, PVA, PVP, dextran, and combinations thereof. The layer 28 can have a thickness of approximately 1 to 500 microns (μm) prior to swelling. In some embodiments, the coating has a thickness of approximately 10 to 100 μm prior to swelling.

Figure 3B:
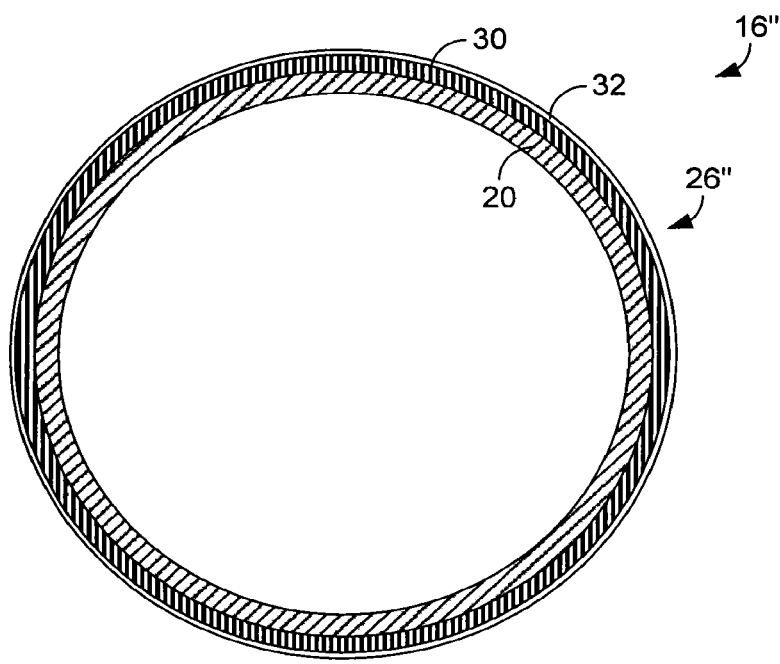
FIG. 3B is a cross-sectional view of a second embodiment for the needle of FIG. 2 taken along line 3-3.

FIG. 3B illustrates a second example coated needle 16". In this embodiment, the shaft 20 is provided with a coating 26" that comprises a first or inner layer 30 composed of a first water-soluble polymer, and a second or outer layer 32 composed of a second water-soluble polymer. As is shown in FIG. 3B, the inner layer 30 is directly applied to the shaft 20 and the outer layer 32 is directly applied to the inner layer. By way of example, the inner layer 30 comprises a polymer selected from the group comprising or consisting of PEO, sodium alginate, PVA, PVP, dextran, and combinations thereof, and the outer layer 30 comprises a different polymer selected from the group comprising or consisting of PEO, sodium alginate, PVA, PVP, dextran, and combinations thereof. In some embodiments, the inner layer 30 comprises PEO and the outer layer 32 comprises PVA. In other embodiments, the inner layer 30 comprises a PEO-sodium alginate mixture and the outer layer 32 comprises PVA. In such a case, the sodium alginate serves as a thickening agent that increases the resistance of the inner layer 30 to backflow when the layer is hydrated.

Surprisingly, multiple layer coatings were determined to be far superior to single layer coatings. Therefore, multiple layers have functional properties that make their use practical. The superior results provided by multiple layer coatings, such as the dual layer coating 26", may be because the outer layer 32 can provide protection to the inner layer 30. In some embodiments, the inner layer 30 provides the bulk of the blocking function because the PEO or PEO-sodium alginate mixture quickly forms a viscous gel when hydrated and the high viscosity of the gel provides great resistance to infusate backflow. The outer layer 32 of PVA hydrates less slowly and therefore shields the inner layer 30 from excess exposure to liquids during insertion, which can cause the inner layer to slide along the shaft 20.

By way of example, the inner layer 30 comprises approximately 50 to 100% weight per volume (w/v) PEO and 0 to 50% w/v sodium alginate. In some embodiments, the inner layer 30 is 80 to 90% w/v PEO and 10 to 20% w/v sodium alginate.

The inner layer 30 can be substantially thicker than the outer layer 32. By way of example, the inner layer 30 can have a thickness that ranges from approximately 1 to 500 µm and the outer layer 32 can have a thickness that ranges from approximately 1 to 100 µm, such that the entire dual layer coating 26" ranges from approximately 2 to 600 µm. In some embodiments, the inner layer 30 has a thickness that ranges from approximately 20 to 30 µm and the outer layer has a thickness that ranges from approximately 4 to 10 µm.

EXAMPLES

Experimental infusions were performed to evaluate the effectiveness of coated needles. For all infusions (n=10), 28 gauge (0.36 mm) stainless steel needles (Hamilton Company, Reno, Nev.) were used. Each needle was initially coated with a 3% w/v PEO (approximately 600,000 MW; Sigma Aldrich, St. Louis, Mo.) and 0.5% w/v sodium alginate (approximately 250 cps; Sigma Aldrich, St. Louis, Mo.) mixture, followed by a outer layer of 7% w/v PVA (approximately 86,000 MW; Acros Organics, Geel, Belgium) solution. The thickness of the PEO and sodium alginate inner layer ranged from approximately 25 to 30 µm and the thickness of the PVA outer layer was less than 6 µm. The thicknesses of the layers and the dual layer coating as a whole, both before and after swelling, are identified in Table 1. As can be appreciated from that table, the dual layer swelled to the extent that its thickness increased approximately 8 to 11 times its original thickness. Each polymer layer was sprayed onto the needles using a gravity feed airbrush (TCP Global, San Diego, Calif.) and dried periodically using a heat gun. After applying the layers, the needles were left to dry overnight in a vacuum oven set to 60° C.

TABLE 1

Polymer Coating Thickness Ranges

| | |
|---|---|
| Inner Layer: Poly(ethylene oxide) & Alginate | 25-30 µm |
| Outer Layer: Poly(vinyl alcohol) | <6 µm |
| Dual Layer: Before Swelling | 30-35 µm |
| Dual Layer: After Swelling | 250-400 µm |

All infusions were conducted in a hydrogel brain tissue phantom prepared using a 0.6% w/v solution of TreviGel™ 5000 powder (Trevigen, Gaithersburg, Md.). The solution was covered and heated to boiling over a hot plate. After boiling, the solution was poured into a 40×60×25 mm acrylic cast and solidified as it approached room temperature. Coated needles were carefully inserted into the hydrogel brain tissue phantom to a distance of 25 mm using a stereotactic guide (Graduated Knob UniSlide, Velmex, Bloomfield, N.Y.) connected to a syringe pump via tubing. After insertion into the target site, the coated needles were allotted 5.5 minutes to enable hydration of the PEO-alginate and PVA coatings. Immediately thereafter, 4.0 microliters (µl) of Evans-Blue labeled albumin (EBA) was infused into the brain phantom at a rate of 0.3 µl min$^{-1}$. Recorded backflow distances for polymer coated needle infusions, shown in Table 2, were calculated using:

$X$=EBA Infusate Distance from Needle Tip−Distribution Radius where the distribution radius accounts for the average radial length of infusate distribution observed after successful infusions without backflow. For each infusion, an image was taken every 30 seconds using a CMOS camera (OptixCam Summit Series OCX-5, Wirtz, Va.) positioned above the brain phantom cast.

TABLE 2

Backflow Distances Along Needle Tract (mm)

| Needle | 1 | 2 | 3 | 4 | 5 | 6 | 7 | 8 | 9 | 10 |
|---|---|---|---|---|---|---|---|---|---|---|
| Distance | 2.0 | 4.3 | 0.4 | 2.7 | 1.5 | 2.0 | 12.0 | 0.8 | 1.3 | 3.5 |

When infusing with control-group uncoated stainless steel needles under the above-specified experimental conditions, infusate backflow consistently exceeded 20 mm from the tip of the needle, giving little to no infusate distribution within the target site. Such infusion is depicted in FIG. 4 in which infusate 40 is shown traveling upward (see arrows) along the outer periphery of the uncoated needle 42. Under the same conditions, the dual layer coating proved to be effective in preventing such backflow and achieving successful distribution, as depicted in FIG. 5. In that figure, the infusate 44 is shown collecting in a target area 46 due to the presence and blocking function of the swollen coating 48 of the needle 50. Of the ten trials performed using the coated needles, the PEO-alginate/PEO coating held backflow to below 2 mm for 60% of infusion trials and reduced backflow to less than 4 mm for 80% of all infusions. Although polymer coating slippage did occur in some insertions, no obvious advantage or disadvantage in preventing backflow was observed from the slipped polymer formation when compared to those trials in which no slippage occurred.

Figure 6:
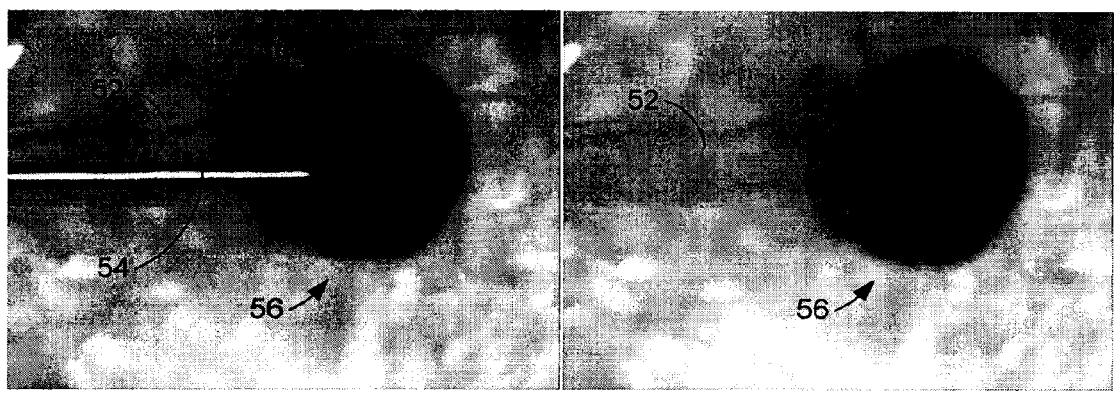
FIG. 6 comprises images illustrating the results of infusing a substance using a coated needle.

Backflow was observed upon removal of uncoated needles from the hydrogel brain phantom after an insertion. That phenomenon did not occur, however, with the coated needles. As is apparent from the images of FIG. 6, the hydrated polymers 52 from the coated needle 54 remained within the needle tract after the needle was withdrawn, forming a resistant plug at the edge of the infusion site 56. This aspect can be readily adapted to sampling or biopsy procedures in which samples must be taken from target sites, such as tumors, without migration to surrounding tissues.

It is further noted that the polymer coatings described herein can be used to deliver drugs to the tissues in which the coated needles are inserted. Such delivery may be enhanced by the swelling behavior of the coating.

The invention claimed is:

1. A system of preventing migration of tissue and migration of a delivered substance through a pathway, comprising:
   a needle comprising an elongated shaft that defines an outer surface; and
   a polymer coating applied to the outer surface of the elongated shaft, the polymer coating being released from the outer surface of the elongated shaft into the tissue to act as a plug to block the pathway formed by insertion of the needle into the tissue following withdrawal of the needle from the tissue, wherein the polymer coating comprises a polymer selected from the group comprising polyethylene oxide (PEO), sodium alginate, polyvinyl alcohol (PVA), polyvinylpyrrolidone (PVP), dextran, and combinations thereof.

2. The system of claim 1, wherein the polymer coating swells upon insertion of the needle into tissue to form a hydrogel that provides a barrier between the needle and the tissue.

3. The system of claim 2, wherein the polymer coating swells to an extent that the polymer coating increases approximately 8 to 11 times its original thickness.

4. The system of claim 1, wherein the elongated shaft has an outer diameter in a range of approximately 0.2 to 2.11 millimeters.

5. The system of claim 1, wherein the polymer coating has a thickness that ranges from approximately 2 to 600 microns.

6. The system of claim 1, wherein the polymer coating acting as the plug can be used to deliver a drug to the tissue.

7. A needle comprising:
an elongated shaft that defines an outer surface; and
a polymer coating applied to the outer surface of the elongated shaft, the polymer coating being released from the outer surface of the elongated shaft into an object to act as a plug and block a tract formed by insertion of the needle into the object following removal of the needle from the object, wherein the polymer coating is applied to the outer surface of the elongated shaft.

8. The needle of claim 7, wherein the polymer coating comprises a polymer selected from the group comprising polyethylene oxide (PEO), sodium alginate, polyvinyl alcohol (PVA), polyvinylpyrrolidone (PVP), dextran, and combinations thereof.

9. The needle of claim 7, wherein the polymer coating is a dual coating comprising an inner layer that is applied to the outer surface of the elongated shaft and an outer layer that is applied to the inner layer, the inner layer comprising a first polymer and the outer layer comprising a second polymer.

10. The needle of claim 9, wherein the inner layer comprises polyethylene oxide (PEO).

11. The needle of claim 9, wherein the inner layer comprises polyethylene oxide (PEO) and sodium alginate.

12. The needle of claim 11, wherein the inner layer comprises approximately 50 to 100% weight per volume polyethylene oxide (PEO) and approximately 0 to 50% weight per volume sodium alginate.

13. The needle of claim 11, wherein the outer layer comprises polyvinyl alcohol (PVA).

14. The needle of claim 9, wherein the inner layer has a thickness that ranges from approximately 1 to 500 microns and the outer layer has a thickness that ranges from approximately 1 to 100 microns.

15. The needle of claim 7, wherein the polymer coating acting as the plug can be used to deliver a drug to the object.

16. A method for delivering a drug to tissue, comprising:
applying a polymer coating to the outer surface of a shaft of a needle;
inserting the needle that is coated into the tissue to release the polymer coating from the outer surface of the shaft;
delivering the drug into the tissue with the needle; and
withdrawing the needle and leaving the polymer coating within a channel formed by the needle to act as a plug, wherein the polymer coating swells when hydrated to form a hydrogel that provides a barrier between the needle and the tissue that prevents a backflow of the drug between the needle and the tissue.

17. The method of claim 16, wherein the needle comprises a cannula.

18. The method of claim 16, wherein applying the polymer comprises applying an inner layer of polyethylene oxide (PEO) and sodium alginate to the shaft of the needle and applying an outer layer of polyvinyl alcohol (PVA) to the inner layer.

19. The method of claim 16, further comprising delivering a second drug to the tissue with the plug.

20. The method of claim 16, wherein the needle is connected to an infusion pump to drive the drug into the tissue.

* * * * *